(12) United States Patent
Toru et al.

(10) Patent No.: US 7,638,654 B2
(45) Date of Patent: Dec. 29, 2009

(54) 1-FLUORO-1,1-BIS-(PHENYLSULFONYL)METHANE AND PRODUCTION METHOD THEREOF

(75) Inventors: Takeshi Toru, Aichi (JP); Norio Shibata, Aichi (JP); Shuichi Nakamura, Aichi (JP); Takeo Fukuzumi, Mie (JP)

(73) Assignees: Nagoya Institute of Technology, Aichi (JP); Tosoh F-Tech, Inc., Yamaguchi (JP)

( * ) Notice: Subject to any disclaimer, the term of this patent is extended or adjusted under 35 U.S.C. 154(b) by 0 days.

(21) Appl. No.: 12/224,664

(22) PCT Filed: Mar. 2, 2007

(86) PCT No.: PCT/JP2007/053997

§ 371 (c)(1),
(2), (4) Date: Dec. 17, 2008

(87) PCT Pub. No.: WO2007/100074

PCT Pub. Date: Sep. 7, 2007

(65) Prior Publication Data

US 2009/0131723 A1    May 21, 2009

(30) Foreign Application Priority Data

Mar. 3, 2006 (JP) .............................. 2006-057330

(51) Int. Cl.
*C07C 315/04* (2006.01)
*C07C 317/14* (2006.01)

(52) U.S. Cl. .......................................... 568/28; 568/34

(58) Field of Classification Search .................... 568/28, 568/34
See application file for complete search history.

(56) References Cited

U.S. PATENT DOCUMENTS 4,562,280 A * 12/1985 Gilpin et al. ................. 560/103
2003/0153778 A1   8/2003 Prakash et al.

FOREIGN PATENT DOCUMENTS

JP   2005-511665   4/2005

WO   03/048033   6/2003

OTHER PUBLICATIONS

Adam et al. A Facile Diastereoselective Synthesis of Functionalized 1,2,3-Trisubstituted Benzocyclopentenes through the Cycloaddition of Bis(phenylsulfonyl) iodonium Ylides to Cylic Alkenes. Journal of Organic Chemistry, 2003, vol. 68, p. 9155 to 9158.*
Hadjiarapoglou et al. Phenyliodonium Bis(phenylsulfonyl) methylide: A New Hypervalent Iodonium Ylide. Journal of the American Chemical Society, 1985, vol. 107, p. 7178 to 7179.*
Makoszka et al. Vicarious Nucleophilic Substitution of Hydrogen in Nitrophenyl Toluenesulfonates. Tetrahedron, vol. 53 (13), pp. 4739 to 4750.*
Ni et al. Nucleophilic Fluoroalkylation of Epoxides with Fluorinted Sulfones. Journal of Organic Chemistry, 2006, vol. 71, pp. 6829 to 6833.*
Fukuzumi et al. Fluorobis(phenylsulfonyl) methane: A Fluoromethide Equivalent and Palladium-Catalyzed Enantioselective Allylic Monofluoromethylation. Angnew. Chemie. Int. Ed. 2006, vol. 45, pp. 4973 to 4977.*
International Search Report dated May 22, 2007 in the International (PCT) Application PCT/JP2007/053997 of which the present application is the U.S. National Stage.
Mieczyslaw Makosza et al., "Vicarious Nucleophilic Substitution of Hydrogen in Nitrophenyl Toluenesulfonates", Tetrahedron, vol. 53, No. 13, pp. 4739-4750, 1997.

* cited by examiner

*Primary Examiner*—Sikarl A Witherspoon
(74) *Attorney, Agent, or Firm*—Wenderoth, Lind & Ponack, L.L.P.

(57) ABSTRACT

A novel 1-fluoro-1,1-bis(arylsulfonyl)methane is provided which is useful in monofluoromethylation. Also provided is a production method thereof.

A method for producing a fluorobis(arylsulfonyl)methane, the method including the steps of: treating a bis(arylsulfonyl)methane represented by the following formula (1), $$(ArSO_2)_2CH_2 \qquad (1)$$

(wherein Ar represents a substituted or unsubstituted phenyl group or naphthyl group)
with a base; and then adding a fluorination reagent thereto, to produce fluorobis(arylsulfonyl)methane represented by the following formula (2)

$$(ArSO_2)_2CHF \qquad (2)$$

(wherein Ar is defined as above), and
a fluorobis(arylsulfonyl)methane (2) represented by the above formula (2), which is a novel compound that is very useful in producing a monofluoromethyl.

3 Claims, No Drawings

1-FLUORO-1, 1-BIS-(PHENYLSULFONYL)METHANE AND PRODUCTION METHOD THEREOF

TECHNICAL FIELD

The present invention relates to novel 1-fluoro-1,1-bis(arylsulfonyl)methane which is useful in monofluoromethylation, and a production method thereof.

BACKGROUND ART

Fluorinated compounds are important in providing featured capabilities in physiologically active substances which are useful as a medical supplies. Currently, although the monofluorination of an activated site, such as an enolate, and monofluorination reactions by a substitution reaction or the like with respect to a halogen are known, monofluoromethylation reactions are not known.

DISCLOSURE OF THE INVENTION

Problems to be Solved by the Invention

It is an object of the present invention to provide novel 1-fluoro-1,1-bis(arylsulfonyl)methane which is useful in monofluoromethylation, and a production method thereof.

Means for Solving the Problem

As a result of intensive research into developing an efficient monofluoromethylation reagent, the present inventor discovered 1-fluoro-1,1-bis(arylsulfonyl)methane.

Specifically, the present invention is a method for producing a fluorobis(arylsulfonyl)methane, the method including the steps of: treating a bis(arylsulfonyl)methane represented by the following formula (1), $$(ArSO_2)_2CH_2 \quad (1)$$

(wherein Ar represents a substituted or unsubstituted phenyl group or naphthyl group)

with a base; and then adding a fluorinating reagent thereto, to produce fluorobis(arylsulfonyl)methane represented by the following formula (2)

$$(ArSO_2)_2CHF \quad (2)$$

(wherein Ar is defined as above), and a fluorobis(arylsulfonyl)methane (2) represented by the above formula (2), which is a novel compound that is very useful in producing a monofluoromethyl group.

EFFECT OF THE INVENTION

The compound of the present invention can be used as a monofluoromethylating reagent.

BEST MODE FOR CARRYING OUT THE INVENTION

The present invention will now be described in more detail.

Fluorobis(arylsulfonyl)methane (2) can be obtained by treating bis(arylsulfonyl)methane with a base to generate a carbanion, and then reacting with a fluorinating reagent. Examples of bases which can be preferably used include $K_2CO_3$, $Li_2CO_3$, $Na_2CO_3$, $NaHCO_3$, NaOH, KOH, RbOH, CsOH, $Cs_2CO_3$, NaH, and KH. The base may be used in an amount of 1 to 10 equivalents based on the bis(arylsulfonyl)methane. Examples of the fluorinating reagent include N-fluorobenzenesulfonimide, N-fluoro-N-methyl-P-toluenesulfonamide, N-fluoro-N'-chloromethyltriethylenediamine bis(tetrafluoroborate) (SELECTFLUOR™), trifluoromethylhypofluorite ($CF_3OF$), acetyl hypofluorite ($CH_3COOF$), perchloryl fluoride ($ClO_3F$), cesium sulfate fluorite ($CsSO_4F$), 1,1'-difluoro-2,2'-bipyridinium bis(tetrafluoroborate), N-fluoro-4,6-dimethylpyridinium 2-sulfonate, N-fluoro-4-methylpyridinium 2-sulfonate, N-fluoro-5-(trifluoromethyl)pyridinium 2-sulfonate, and N-fluoro-4,6-bis(trifluoromethyl)pyridinium 2-sulfonate. 1 to 10 equivalents of the fluorinating reagent is preferred to use. The reaction is performed in an organic solvent, and examples thereof may include methylene chloride, chloroform, 1,2-dichloroethane, toluene, benzene, hexane, pentane, tetrahydrofuran diethylether, t-butylethyl ether, dimethylformamide, dimethyl sulfoxide, acetonitrile, methanol, and ethanol.

Fluorobis(arylsulfonyl)methane (2) is useful as a monofluoromethylating reagent. Specifically, the fluorobis(arylsulfonyl)methylated reactant (4) can be obtained by treating (2) with a base to generate a carbanion, and then subjecting this to a nucleophilic reaction with the compound (3) shown below. (4) can be easily converted into the monofluoromethylated reactant by subjecting it to a desulfonylating reaction. Attention should be paid to the point that an optically active fluorobis(arylsulfonyl)methylated reactant (4) can be obtained by reacting the carbanion derived from the fluorobis(arylsulfonyl)methane (2) with various catalysts using an optically active ligand. Furthermore, this fluorobis(arylsulfonyl)methylated reactant can be derived to an optically active monofluoromethylated compound through a desulfonylating reaction. Specifically, the fluorobis(arylsulfonyl)methane (2) is an excellent reagent which is capable of deriving an optically active monofluoromethylated compound as its carbanion by a nucleophilic reaction and a desulfonylation reaction. This can also be referred to as a previously unknown fluoromethyl anion equivalent.

Examples of the bis(arylsulfonyl)methane (1) include, but are not limited to, bis(phenylsulfonyl)methane, bis(4-methylphenylsulfonyl)methane, bis(2-methylphenylsulfonyl)methane, bis(3-methylphenylsulfonyl)methane, bis(3-methoxyphenylsulfonyl)methane, bis(4-methoxyphenylsulfonyl)methane, bis(2-methoxyphenylsulfonyl)methane, bis(4-ethylphenylsulfonyl)methane, bis(3-ethylphenylsulfonyl)methane, bis(2-ethylphenylsulfonyl)methane, bis(2,4,6-trimethylphenylsulfonyl)methane, bis(2,4,6-triisopropylphenylsulfonyl)methane, bis(4-chlorophenylsulfonyl)methane, bis(3-chlorophenylsulfonyl)methane, bis(2-chlorophenylsulfonyl)methane, bis(4-bromophenylsulfonyl)methane, bis(3-bromophenylsulfonyl)methane, bis(2-bromophenylsulfonyl)methane, bis(4-nitrophenylsulfonyl)methane, bis(4-t-butylphenylsulfonyl)methane, and bis(3,5-di-t-butyl-4-methoxyphenysulfonyl)methane.

[Chemical formula 1]

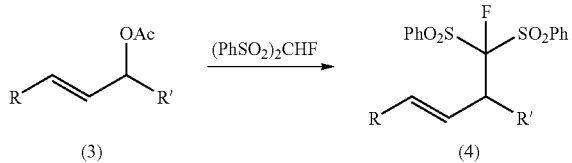

Examples of the compound (3) include allyl compounds, carbonyl compounds, α,β-unsaturated carbonyl compounds, imines, and halogenated alkanes. Specific examples include allylacetate compounds which may be substituted, and preferred allylacetates include, but are of course not limited to, 1-acetoxy-1,3,-diphenylpropene, 1-acetoxy-1,3,-bis(4-isobutylphenyl)propene, 1-acetoxy-1,3,-bis(4-isobutylphenyl)propene, 1-acetoxy-1,3,-bis(4-isobutylphenyl)propene, 1-acetoxy-1,3,-bis(4-methylphenyl)propene, 1-acetoxy-1,3,-bis(4-butylphenyl)propene, 1-acetoxy-1,3,-bis(4-propylphenyl)propene, 1-acetoxy-1,3,-bis(4-octylphenyl)propene, 1-acetoxy-1,3,-bis(2,4-dimethylphenyl)propene, 1-acetoxy-1,3,-di(1-naphthyl)propene, 1-acetoxy-1,3,-di(2-naphthyl)propene, 1-acetoxy-3-phenylpropene, and 4-acetoxyhex-2-ene.

The allyl acetate compound and the catalyst are reacted, and then, in the presence of a base, the resultant product is further reacted with fluorobis(arylsulfonyl)methane (2), whereby the fluorobis(arylsulfonyl)methylated reactant (4) can be obtained. Here, it is preferred to use a palladium catalyst as the catalyst. Examples of the palladium catalyst include an allylpalladium(II) chloride dimer, bis(triphenylphosphine)palladium(II) dichloride, trans-benzyl (chloro)bis(triphenylphosphine)palladium(II), bis(acetonitrile) dichloropalladium(II), bis(benzonitrile)palladium(II) chloride, bis(triphenylphosphine)palladium(II) diacetic acid, cis-dichlorobis(dimethylphenylphosphine) palladium(II), dichloro(N,N,N',N'-tetraethylenediamine)palladium(II), dichlorobis(triethylphosphine)palladium(II), palladium(II) acetate, palladium(II) acetylacetonate, and palladium(II) cyanide. These catalysts are usually used with an achiral or a chiral ligand. The ligand may be used in an amount of 1 equivalent based on the palladium. Examples of the achiral ligand include triphenyl phosphine, 1,2-bis(diphenylphosphine)methane, 1,2-bis(diphenylphosphine) ethane, 1,2-bis(diphenylphosphine) propane, 1,2-bis(diphenylphosphine) butane, and 1,2-bis(diphenylphosphine)ferrocene. Examples of the chiral catalyst include (R)-2-[2-(diphenylphosphino)phenyl]-4-phenyl-2-oxazoline, (R)-1'-binaphthyl-2.2'-diphenylphosphine, [1,1'-naphthalene]-2,2'-diylbis[bis(4-methylphenyl)phosphine, 2,2'-isopropylidene[(4S)-4-phenyl-2-oxazoline] (Box-Ph), [4,4'-bis-1,3-benzodioxole]-5,5'-diyl-1-bis(diphenylphosphine) (SEGPROS), 1,2-bis[(2S,5S)-2,5-dimethylphospholano]ethane (BPE), (R,R)-(−)-1,2-bis{(R)-4,5-dihydro-3H-binaphtho[1,2-c:2',1'-E]phosphino}benzene (Binaphane), 1,2-ethanediylbis[(2-methoxyphenyl)phenylphosphine (DIPAMP), [(1R,2S)-1,2-dimethyl-1,2-ethanediyl]bis[diphenylphosphine (CHIRAPHOS), (2R,3R)-bicyclo[2.2.1]hept-5-ene-2,3-diyl-bisdiphenylphosphine (NORPHOS), and [(2,2-dimethyl-1,3-dioxolane-4,5-diyl)bis(methylene)]bisdiphenylphosphine (DIOP). Although the catalyst is used in an amount in the range of 0.01 mol % to 20 mol %, it preferred to use in the range of 0.1 mol % to 10 mol %. If a chiral ligand is used, a chiral fluorobis(arylsulfonyl)methylated reactant (4) can be obtained.

Examples of bases which may be preferably used include $K_2CO_3$, $Li_2CO_3$, $Na_2CO_3$, $NaHCO_3$, NaOH, KOH, RbOH, CsOH, $Cs_2CO_3$, NaH, and KH. The reaction is performed in an organic solvent, and examples thereof may include $CH_2Cl_2$, $CHCl_3$, $ClCH_2CH_2Cl$, toluene, benzene, hexane, pentane, tetrahydrofuran diethylether, t-butylethyl ether, dimethylformamide, dimethyl sulfoxide, acetonitrile, methanol, and ethanol.

The reaction is usually carried out in a range of −50 to 80° C., although it is preferred to carry out in a range of −20 to 40° C. After the reaction is completed, the crude reaction product is isolated by a usually carried out method, and then a purified product (4) can be prepared by methods such as column chromatography, distillation, and recrystallization as necessary.

The fluorobis(arylsulfonyl)methane (2) which constitutes the present invention has the unique feature that it can be used to obtain a chiral fluorobis(arylsulfonyl)methylated reactant product (4) by using a chiral catalyst. Furthermore, the fluorobis(arylsulfonyl)methylated reaction product (4) has the excellent feature that it can be easily converted into a monofluoromethylated reaction product by subjecting it to dearylsulfonylation. It is preferred to carry out the dearylsulfonylation, for example, by reacting with magnesium in methanol. In addition, it is particularly worth mentioning that, at this reaction stage, the chiral fluorobis(arylsulfonyl)methylated reaction product (4) can be converted into the monofluoromethylated reaction product with hardly any reduction in its optical purity, namely, without causing any racemization.

In addition to allyl acetate derivatives, the below-illustrated fluorobis(arylsulfonyl)methylated reaction products can also be obtained. Specific examples include a β-addition reaction into an α,β-unsaturated carbonyl compound (reaction formula 1), an additional reaction into a ketone or an aldehyde (reaction formula 2), and an additional reaction into an imine (reaction formula 3). Although a suitable base can be used for these reactions, examples thereof may include triethylamine, diisopropylethylamine, DBU, 1,4-diazabicyclo[2,2,2]octane, DABCO, pyridine, sodium methoxide, sodium ethoxide, sodium t-butoxide, kinin, quinidine, cinchonine, and cinchonidine. It is preferred to use a catalyst, and examples thereof may include N-benzyl cinchonidium bromide, (L)-proline, 1,3-diphenyl-2-thiourea, a BINOL-Al complex (ALB), a BINOL-Ti complex, Box-Ph, (S,S)—N,N'-bis(3,5-di-t-butylsalicylidene)-1,2-cyclohexanediamine, $K_2CO_3$, $TiCl_4$, $SnCl_4$, $AlCl_3$, $Cu(OTf)_2$, $MgCl_2$, $NiClO_4H_2O$, $Pd(OAc)_2$, $PPh_3$, dppe, dppp, and dppb. The reaction may be carried out by using a commonly-used organic solvent, for example, $CH_2Cl_2$, $CHCl_3$, $ClCH_2CH_2Cl$, toluene, benzene, hexane, THF, $Et_2O$, DMF, DMSO, and $CH_3CN$ and the like, with the catalyst and the base.

[Chemical formula 2]

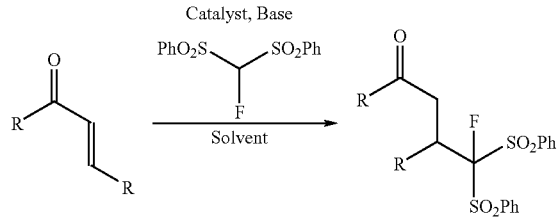

Reaction formula 1

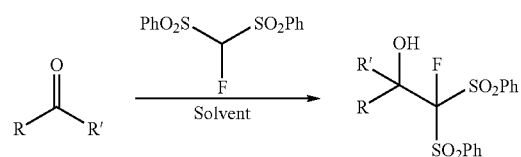

Reaction formula 2

-continued

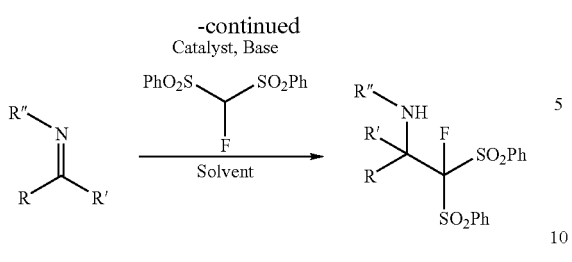

Reaction formula 3

The thus-obtained fluorobis(arylsulfonyl)methylated reactant can be easily converted into a monofluoromethylated reactant by subjecting it to adesulfonylation reaction as necessary.

The following examples will now be illustrated to describe the present invention more specifically. However, the present invention is not limited to the following examples.

EXAMPLE 1

Synthesis of 1-fluoro-1,1-bis(phenylsulfonyl)methane

[Chemical formula 3]

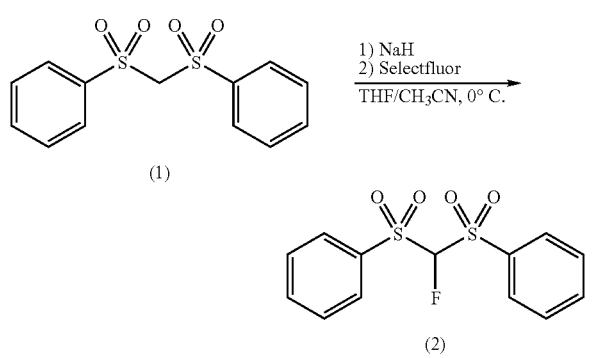

A 40 mL solution of a 60% oil dispersion of sodium hydride (205.3 mg, 0.833 mmol, 1.0 eq) in tetrahydrofuran was cooled to 0° C., and then charged with bis(phenylsulfonyl)methane (241 mg, 0.813 mmol, 1.0 eq). The solution was stirred at room temperature for 1 hour. The obtained suspension was charged at 0° C. into a 50 mL solution of Selectfluor (N-fluoro-N'-chloromethyl-triethylenediamine bis(tetrafluoroborate)) (33.3 mg, 0.833 mmol, 1.0 eq) in acetonitrile, and the solution was stirred at room temperature for 1 hour. The reactant solution was then charged with saturated aqueous ammonium chloride solution. The aqueous layer was extracted with methylene chloride and then the extract was dried with anhydrous sodium sulfate. The solvent was removed under reduced pressure by distillation, and then the resultant product was purified by column chromatography (hexane:methylene chloride=2:8) to obtain 195 mg (57%) of (2) as a white solid.

$^1$H NMR (200 MHz; CDCl$_3$) δ 5.70 (1H, d, J=45.8 Hz, CH), 7.55-7.65 (4H, m, Ar), 7.70-7.80 (2H, m, Ar), 7.95-8.05 (4H, d, Ar) $^{19}$F NMR (188 MHz; CDCl$_3$) δ 167.2 (d, J=14.8 Hz) MS (ESI-TOF) 314 (M$^+$), 173 (M$^+$-SO$_2$Ph), 141 (M$^+$-PhSO$_2$CHF)

EXAMPLE 2

1-Fluoro-1,1-bis(phenylsulfonyl)methylation reaction

[Chemical formula 4]

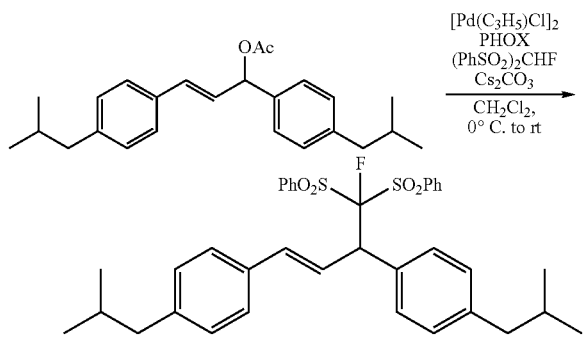

(4S)-2-(2-diphenylphosphinophenyl)-4-isopropyl-1,3-oxazoline (2.5 mg, 0.0067 mmol, 5 mol %), [Pd(C$_3$H$_5$)Cl]$_2$ (1.2 mg, 0.0033 mmol, 2.5 mol %), and acetic acid (2E)-1,3-bis (4-isobutylphenyl)-2-propenyl (99.1 mg, 0.272 mmol, 2.0 eq) were stirred at room temperature for 15 minutes in methylene chloride. The solution was cooled to 0° C., and then charged with 1-fluoro-1,1-bis(phenylsulfonyl)methane (42.6 mg, 0.136 mmol, 1.0 eq) and Cs$_2$CO$_3$ (87.8 mg, 0.270 mmol, 2.0 eq). The solution was stirred at 0° C. for 60 hours. The reactant solution was then charged with saturated aqueous ammonium chloride solution. The aqueous layer was extracted with methylene chloride and then the extract was dried with anhydrous sodium sulfate. The solvent was removed under reduced pressure by distillation, and then the reactant was purified by column chromatography (hexane: ethyl acetate=8:2) to obtain (E)-4-fluoro-1,3-bis(4-isobutylphenyl)-4,4-bis(phenylsulfonyl) but-1-ene as a yellow solid (77 mg, 91%, 98% ee).

HPLC(CHIRALCEL AD-H, Hexane/$^i$PrOH=80:20, 1.0 ml/min, 10.0 min and 15.2 min)

$^1$H NMR (200 MHz; CDCl$_3$) δ 0.88 (12H, t, J=5.8 Hz, CH$_3$), 1.71-1.92 (2H, m, CH), 2.38 (2H, d, J=7.2 Hz, CH$_2$), 2.45 (2H, d, J=7.0 Hz, CH$_2$), 4.70 (1H, dd, J=9.6, 14.5 Hz, CH=CH—CH), 6.46 (1H, d, J=15.8 Hz, CH=CH—CH), 6.98-7.90 (19H, m, CH=CH—CH, Ar) $^{13}$C NMR (50 MHz; CDCl$_3$) δ 127.8 (d, J=14.5 Hz) 14.3, 21.1, 30.1, 30.3, 45.0, 45.2. 51.1, 51.4, 60.3, 116.4, 119.0, 121.6, 121.7, 126.3, 128.1, 128.3, 128.5, 129.0, 130.0, 130.7, 132.4, 134.0, 134.4, 135.5, 136.0, 136.7, 141.0, 141.2 $^{19}$F NMR (188 MHz; CDCl$_3$) δ 127.8 (d, J=14.5 Hz)

EXAMPLE 3

1-Fluoro-1,1-bis(phenylsulfonyl)methylation reaction (4S)-2-(2-diphenylphosphinophenyl)-4-isopropyl-1,3-oxazoline (2.5 mg, 0.0067 mmol, 5 mol %), [Pd(C$_3$H$_5$)Cl]$_2$ (1.3 mg, 0.0036 mmol, 2.5 mol %), and acetic acid (2E)-1,3-bis (4-isobutylphenyl)-2-propenyl (50.2 mg, 0.138 mmol, 1.0 eq)

were stirred at room temperature for 15 minutes in trifluoromethylbenzene. The solution was cooled to 0° C., and then charged with 1-fluoro-1,1-bis(phenylsulfonyl)methane (47.9 mg, 0.152 mmol, 1.1 eq) and $Cs_2CO_3$ (49.3 mg, 0.151 mmol, 1.1 eq). The solution was stirred at 0° C. for 10 hours. The reactant solution was then charged with saturated aqueous ammonium chloride solution. The aqueous layer was extracted with methylene chloride and then the extract was dried with anhydrous sodium sulfate. The solvent was removed under reduced pressure by distillation, and then the reactant was purified by column chromatography (hexane:ethyl acetate=8:2) to obtain (E)-4-fluoro-1,3-bis(4-isobutylphenyl)-4,4-bis(phenylsulfonyl) but-1-ene as a yellow solid (12.0 mg, 14%, 97% ee).

EXAMPLE 4

1-Fluoro-1,1-bis(phenylsulfonyl)methylation reaction (4S)-2-(2-diphenylphosphinophenyl)-4-isopropyl-1,3-oxazoline (2.6 mg, 0.0070 mmol, 5 mol %), $[Pd(C_3H_5)Cl]_2$ (1.4 mg, 0.0038 mmol, 2.5 mol %), and acetic acid (2E)-1,3-bis(4-isobutylphenyl)-2-propenyl (50.8 mg, 0.139 mmol, 1.0 eq) were stirred at room temperature for 15 minutes in chloroform. The solution was cooled to 0° C., and then charged with 1-fluoro-1,1-bis(phenylsulfonyl)methane (47.4 mg, 0.151 mmol, 1.1 eq) and $Cs_2CO_3$ (49.5 mg, 0.152 mmol, 1.1 eq). The solution was stirred at 0° C. for 24 hours. The reactant solution was then charged with saturated aqueous ammonium chloride solution. The aqueous layer was extracted with methylene chloride and then the extract was dried with anhydrous sodium sulfate. The solvent was removed under reduced pressure by distillation, and then the resultant product was purified by column chromatography (hexane:ethyl acetate=8:2) to obtain (E)-4-fluoro-1,3-bis(4-isobutylphenyl)-4,4-bis(phenylsulfonyl) but-1-ene as a yellow solid (5.8 mg, 8%, 97% ee).

EXAMPLE 5

1-Fluoro-1,1-bis(phenylsulfonyl)methylation reaction (4S)-2-(2-diphenylphosphinophenyl)-4-isopropyl-1,3-oxazoline (2.7 mg, 0.0072 mmol, 5 mol %), $[Pd(C_3H_5)Cl]_2$ (1.5 mg, 0.0041 mmol, 2.5 mol %), and acetic acid (2E)-1,3-bis(4-isobutylphenyl)-2-propenyl (81.9 mg, 0.225 mmol, 1.5 eq) were stirred at room temperature for 15 minutes in THF. The solution was cooled to 0° C., and then a solution of 1-fluoro-1,1-bis(phenylsulfonyl)methane (47.0 mg, 0.150 mmol, 1.0 eq) and NaH (9.2 mg, 0.230 mmol, 1.5 eq) in THF was added dropwise thereto. The solution was stirred at 0° C. for 24 hours. The reactant solution was then charged with saturated aqueous ammonium chloride solution. The aqueous layer was extracted with methylene chloride and then the extract was dried with anhydrous sodium sulfate. The solvent was removed under reduced pressure by distillation, and then the resultant product was purified by column chromatography (hexane:ethyl acetate=8:2) to obtain (E)-4-fluoro-1,3-bis(4-isobutylphenyl)-4,4-bis(phenylsulfonyl) but-1-ene as a yellow solid (19.9 mg, 21%, 95% ee).

EXAMPLE 6

1-Fluoro-1,1-bis(phenylsulfonyl)methylation reaction 2,2'-Bis(2-diphenylphosphino)-1,1'binaphthyl (4.8 mg, 0.0077 mmol, 5 mol %), $[Pd(C_3H_5)Cl]_2$ (1.6 mg, 0.0044 mmol, 2.5 mol %), and acetic acid (2E)-1,3-bis(4-isobutylphenyl)-2-propenyl (109.6 mg, 0.301 mmol, 2.0 eq) were stirred at room temperature for 15 minutes in methylene chloride. The solution was cooled to 0° C., and then charged with 1-fluoro-1,1-bis(phenylsulfonyl)methane (46.9 mg, 0.149 mmol, 1.0 eq) and $Cs_2CO_3$ (98.4 mg, 0.302 mmol, 2.0 eq). The solution was stirred at 0° C. for 48 hours. The reactant solution was then charged with saturated aqueous ammonium chloride solution. The aqueous layer was extracted with methylene chloride and then the extract was dried with anhydrous sodium sulfate. The solvent was removed under reduced pressure by distillation, and then the reactant was purified by column chromatography (hexane:ethyl acetate=8:2) to obtain (E)-4-fluoro-1,3-bis(4-isobutylphenyl)-4,4-bis(phenylsulfonyl) but-1-ene as a yellow solid (80.3 mg, 87%, 88% ee).

EXAMPLE 7

1-Fluoro-1,1-bis(phenylsulfonyl)methylation reaction (4S)-2-(2-diphenylphosphinophenyl)-4-isopropyl-1,3-oxazoline (3.6 mg, 0.0096 mmol, 5 mol %), $[Pd(C_3H_5)Cl]_2$ (1.8 mg, 0.0049 mmol, 2.5 mol %), and acetic acid (2E)-1,3-bis(4-isobutylphenyl)-2-propenyl (74.5 mg, 0.204 mmol, 1.0 eq) were stirred at room temperature for 15 minutes in methylene chloride. The solution was cooled to 0° C., and then charged with 1-fluoro-1,1-bis(phenylsulfonyl)methane (70.6 mg, 0.225 mmol, 1.1 eq) and $K_2CO_3$ (30.8 mg, 0.223 mmol, 1.1 eq). The solution was stirred at 0° C. for 14 hours. The reactant solution was then charged with saturated aqueous ammonium chloride solution. The aqueous layer was extracted with methylene chloride and then the extract was dried with anhydrous sodium sulfate. The solvent was removed under reduced pressure by distillation, and then the resultant product was purified by column chromatography (hexane:ethyl acetate=8:2) to obtain (E)-4-fluoro-1,3-bis(4-isobutylphenyl)-4,4-bis(phenylsulfonyl) but-1-ene as a yellow solid (40 mg, 31%, 94% ee).

EXAMPLE 8

1-Fluoro-1,1-bis(phenylsulfonyl)methylation reaction (4S)-2-(2-diphenylphosphinophenyl)-4-isopropyl-1,3-oxazoline (2.3 mg, 0.0062 mmol, 5 mol %), $[Pd(C_3H_5)Cl]_2$ (1.3 mg, 0.0036 mmol, 2.5 mol %), and acetic acid (2E)-1,3-bis(4-isobutylphenyl)-2-propenyl (50.6 mg, 0.139 mmol, 1.0 eq) were stirred at room temperature for 15 minutes in toluene. The solution was cooled to 0° C., and then charged with 1-fluoro-1,1-bis(phenylsulfonyl)methane (48.2 mg, 0.153 mmol, 1.1 eq) and $Cs_2CO_3$ (49.8 mg, 0.153 mmol, 1.1 eq). The solution was stirred at 0° C. for 8 hours. The reactant solution was then charged with saturated aqueous ammonium chloride solution. The aqueous layer was extracted with methylene chloride and then the extract was dried with anhydrous sodium sulfate. The solvent was removed under reduced pressure by distillation, and then the resultant product was purified by column chromatography (hexane:ethyl acetate=8:2) to obtain (E)-4-fluoro-1,3-bis(4-isobutylphenyl)-4,4-bis(phenylsulfonyl) but-1-ene as a yellow solid (8.8 mg, 10%, 96% ee).

EXAMPLE 9

1-Fluoro-1,1-bis(phenylsulfonyl)methylation reaction

Synthesis of (E)-4-fluoro-1,3-diphenyl-4,4-bis(phenylsulfonyl)but-1-ene

[Chemical formula 5]

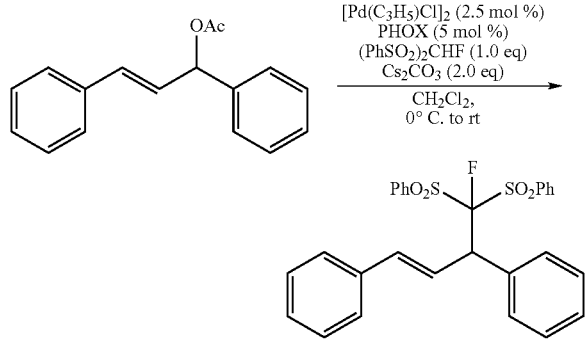

(4S)-2-(2-diphenylphosphinophenyl)-4-isopropyl-1,3-oxazoline (3.5 mg, 0.00937 mmol, 5 mol %), [Pd(C$_3$H$_5$)Cl]$_2$ (1.8 mg, 0.0049 mmol, 2.5 mol %), and acetic acid (E)-1,3-diphenylallyl (50.5 mg, 0.200 mmol, 1.0 eq) were stirred at room temperature for 15 minutes in 1,2-dichloroethane. The solution was cooled to 0° C., and then charged with 1-fluoro-1,1-bis(phenylsulfonyl)methane (68.6 mg, 0.218 mmol, 1.1 eq) and Cs$_2$CO$_3$ (71.2 mg, 0.219 mmol, 1.1 eq). The solution was stirred at 0° C. for 2 hours. The reactant solution was then charged with saturated aqueous ammonium chloride solution. The aqueous layer was extracted with methylene chloride and then the extract was dried with anhydrous sodium sulfate. The solvent was removed under reduced pressure by distillation, and then the resultant product was purified by column chromatography (hexane:methylene chloride=3:7) to obtain (E)-4-fluoro-1,3-diphenyl-4,4-bis(phenylsulfonyl) but-1-ene as a white solid (33.4 mg, 33%, 91% ee).

$^1$H NMR (200 MHz; CDCl$_3$) δ 4.72 (1H, dd, J=9.2, 14.5 Hz, CH=CH—CH), 6.49 (1H, d, J=15.8 Hz, CH=CH—CH), 7.00-7.90 (21H, m, CH=CH—CH, Ar) $^{19}$F NMR (188 MHz; CDCl$_3$) δ 128.5 (d, J=14.5 Hz)

EXAMPLE 10

Synthesis of 3-fluoro-2-(4-isobutylphenyl)-3,3-bis(phenylsulfonyl)propan-1-ol

[Chemical formula 6]

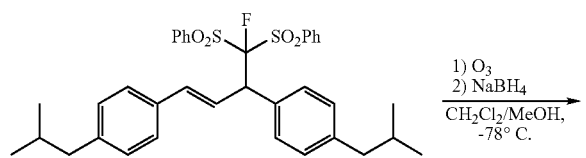

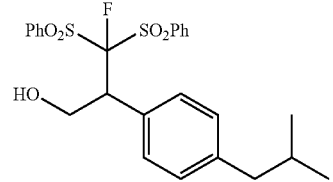

A solution of (E)-4-fluoro-1,3-bis(4-isobutylphenyl)-4,4-bis(phenylsulfonyl) but-1-ene (5a, 506 mg, 0.818 mmol, 1.0 eq) in 20 mL of MeOH and 7 mL of CH$_2$Cl$_2$ was cooled to −78° C. Ozone gas generated by an ozone generator was introduced to this solution for 30 minutes, and then O$_2$ was introduced for 5 minutes to remove excess ozone. Next, the solution was charged with NaBH$_4$ (93.1 mg, 2.49 mmol, 3.0 eq), and the temperature was increased over two hours to room temperature. The reactant solution was then charged with saturated aqueous ammonium chloride solution. The aqueous layer was extracted with methylene chloride and then the extract was dried with anhydrous sodium sulfate. The solvent was removed under reduced pressure by distillation, and then the reactant was purified by column chromatography (hexane:ethyl acetate=6:4) to obtain 3-fluoro-2-(4-isobutylphenyl)-3,3-bis(phenylsulfonyl)propan-1-ol as a white solid (393 mg, 98%).

$^1$H NMR (200 MHz; CDCl$_3$) δ 0.88 (6H, d, J=6.6 Hz, CH$_3$), 1.70-1.90 (1H, m, CH), 2.19 (1H, t, J=6.2 Hz, OH), 2.39 (2H, d, J=7.2 Hz, CH$_2$), 3.95-4.10 (1H, m, CH), 4.42-4.60 (1H, m, CHH), 4.68-4.84 (1H, m, CHH), 6.90-7.10 (4H, m, Ar), 7.40-7.60 (4H, m, Ar), 7.60-7.80 (6H, m, Ar) $^{19}$F NMR (188 MHz; CDCl$_3$) δ 129.7 (d, J=9.2 Hz)

EXAMPLE 11

Desulfonylation Reaction

[Chemical formula 7]

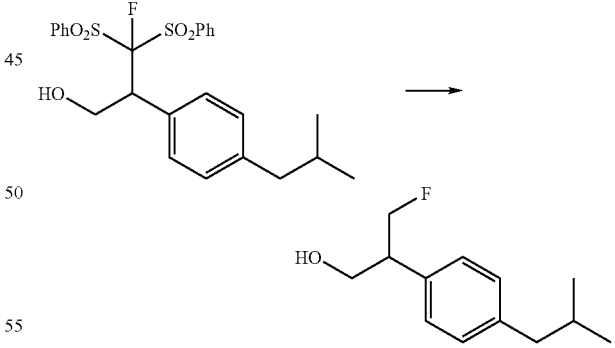

One drop of CH$_2$Br$_2$ and then 1 drop of TMSCl were charged into a 5 mL solution of magnesium ribbon (707 mg, 29.1 mmol, 45.0 eq) in MeOH. The solution was cooled to 0° C., and then a 5 mL solution of 3-fluoro-2-(4-isobutylphenyl)-3,3-bis(phenylsulfonyl)propan-1-ol (317 mg, 0.646 mmol, 1.0 eq) in MeOH was added dropwise thereto. The solution was stirred for 2 hours at 0° C., and then water was charged thereto to stop the reaction. The aqueous solution was acidified using 1 M HCR. The aqueous layer was extracted with methylene chloride and then the extract was dried with anhydrous sodium sulfate. The solvent was removed under reduced pressure by distillation, and then the resultant product was purified by column chromatography (hexane:ethyl acetate=7:3) to obtain 3-fluoro-2-(4-isobutylphenyl)propan-1-ol (119 mg, 87%).

$^1$H NMR (200 MHz; CDCl$_3$) δ 0.90 (6H, d, J=6.6 Hz, CH$_3$), 1.55 (1H, br, OH), 1.74-1.95 (1H, m, CH), 2.44 (2H, d, J=7.2 Hz, CH$_2$), 3.05-3.30 (1H, dm, J=19.8 Hz, CHCH$_2$F), 4.69 (2H, dd, J=5.6, 47.2 Hz, CH$_2$F), 7.00-7.20 (4H, m, Ar) $^{19}$F NMR (188 MHz; CDCl$_3$) δ 8.15 (dt, J=19.8, 47.2 Hz) MS (ESI-TOF) 210 (M$^+$), 179 (M$^+$—CH$_2$OH), 160 (M$^+$—CH$_2$OH, F)

The invention claimed is:

1. A method for producing a fluorobis(arylsulfonyl)methane, the method comprising the steps of: treating a bis(arylsulfonyl)methane represented by the following formula (1), $$(ArSO_2)_2CH_2 \tag{1}$$

(wherein Ar represents a substituted or unsubstituted phenyl group or naphthyl group) with a base; and then adding a fluorination reagent thereto, to produce fluorobis(arylsulfonyl)methane represented by the following formula (2)

$$(ArSO_2)_2CHF \tag{2}$$

(wherein Ar is defined as above).

2. A fluorobis(arylsulfonyl)methane represented by the formula (2) according to claim 1.

3. Fluorobis(phenylsulfonyl)methane represented by the formula (2) according to claim 1, where Ar is a phenyl group.

* * * * *